United States Patent [19]

Sangokoya

[11] Patent Number: 5,670,682
[45] Date of Patent: Sep. 23, 1997

[54] LIQUID CLATHRATE ALUMINOXANE COMPOSITIONS

[75] Inventor: Samuel A. Sangokoya, Baton Rouge, La.

[73] Assignee: Albemarle Corporation, Richmond, Va.

[21] Appl. No.: 546,285

[22] Filed: Oct. 19, 1995

[51] Int. Cl.$^6$ .................................................. C07F 5/06
[52] U.S. Cl. .......................... 556/181; 556/179; 556/187
[58] Field of Search ............................... 556/187, 179, 556/181

[56] References Cited

U.S. PATENT DOCUMENTS

| | | | |
|---|---|---|---|
| 4,024,170 | 5/1977 | Atwood | 260/438.5 R |
| 5,041,583 | 8/1991 | Sangokoya | 556/179 |
| 5,099,050 | 3/1992 | Sangokoya | 556/179 |
| 5,106,804 | 4/1992 | Bailly et al. | 502/108 |
| 5,157,137 | 10/1992 | Sangokoya | 556/179 |
| 5,329,032 | 7/1994 | Tran et al. | 556/179 |
| 5,527,930 | 6/1996 | Sangokoya | 556/179 |

FOREIGN PATENT DOCUMENTS 0644206  3/1995  European Pat. Off. .

OTHER PUBLICATIONS

Atwood, J. L., Coordination Chemistry of Aluminum, Chater 6 pp. 197–224, VCH Publishers Inc. (1993).
Robinson, G. H., Coordination Chemistry Reviews, 112 (1992) pp. 227–245.
Sangokoya, S. A., J. Ind. Phenom., 6(1988) pp. 263–266.

*Primary Examiner*—Porfirio Nazario-Gonzalez
*Attorney, Agent, or Firm*—Philip M. Pippenger

[57] ABSTRACT

Stable liquid clathrate aluminoxane compositions are obtained by the reaction, in aromatic solvents, of aluminoxanes such as, methylaluminoxane, with organic, inorganic or organometallic compounds, such as salts, which can dissociate or partially dissociate into cationic and anionic species (M-X species).

7 Claims, 1 Drawing Sheet

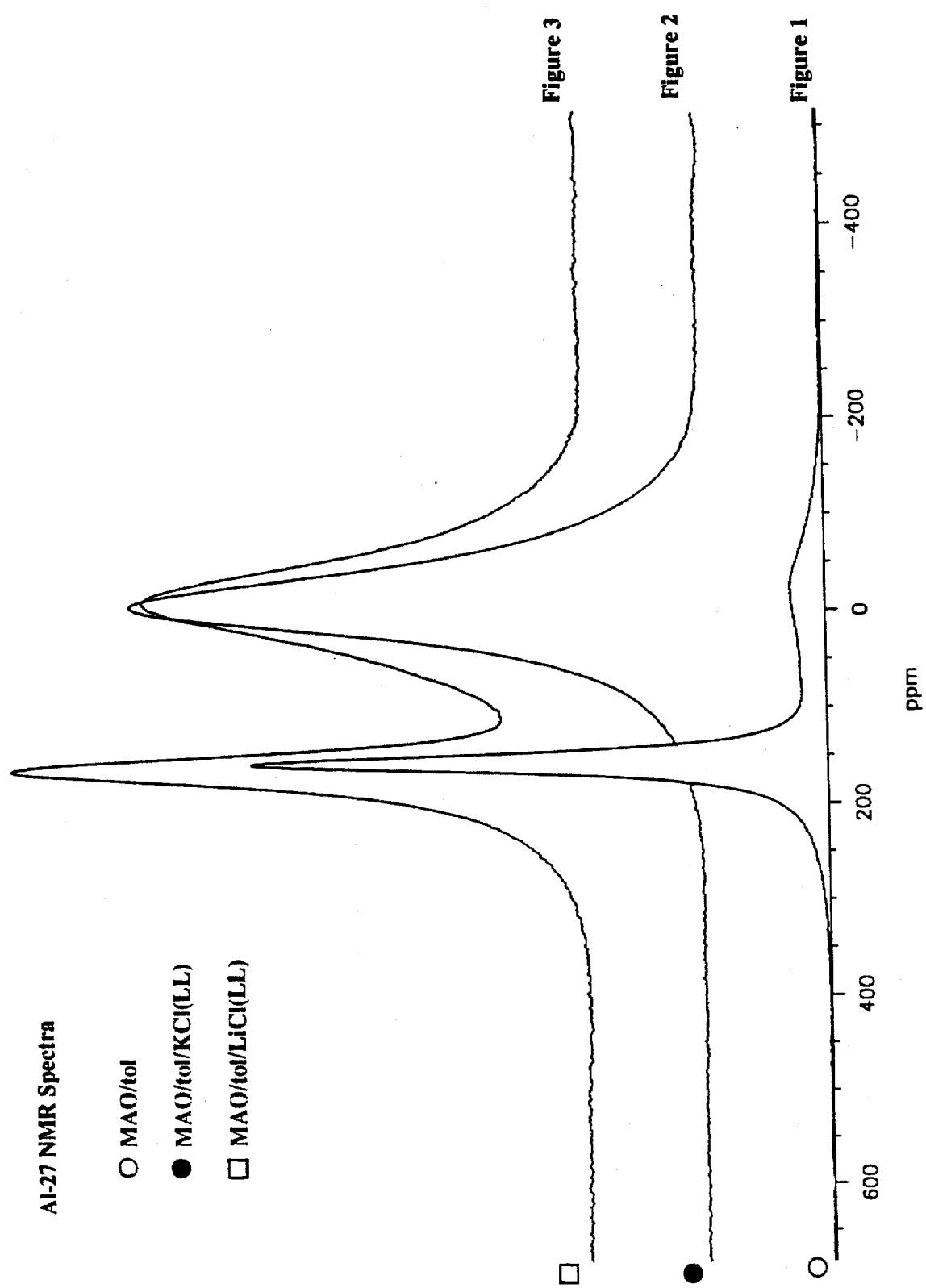

LIQUID CLATHRATE ALUMINOXANE COMPOSITIONS

This invention relates generally to aluminoxane compositions and more specifically to stable, liquid clathrate aluminoxane compositions obtained by the reaction in aromatic solvents of aluminoxanes, especially methylaluminoxane, with organic or inorganic compounds, especially salts which can dissociate or partially dissociate into cationic and anionic species (M-X species). In another aspect, the invention relates to insoluble solid aluminoxane-MX salt compositions. Furthermore, the invention relates to polymerization catalyst compositions which could optionally be supported on inert solid carriers.

Aluminoxanes are generally prepared by the hydrolysis of aluminum alkyls either by direct water addition or by treatment with salt hydrates. Aluminoxanes are used in combination with various types of metallocenes and/or transition metal compounds to catalyze olefin oligomerization and polymerization. These catalyst components can be supported on solid carriers such as metal oxides, for example silica or alumina, for use in heterogeneous and gas phase polymerizations.

Methylaluminoxane (MAO) is the most useful of all aluminoxanes for polymerization applications. However, certain limitations are associated with regular methylaluminoxane solutions. Such limitations include poor solubility, especially in aliphatic solvents, instability, and gel formation.

The present invention relates to the alleviation of most if not all of the present problems associated with the industrial use of methylaluminoxanes as co-catalyst components.

A copending U.S. patent application Ser. No. 08/452,170, filed May 26, 1995, describes the formation of aluminoxanate compositions which are the reaction products of aluminoxanes, such as methylaluminoxane, and certain salts of polyoxy-compounds such as sodium aluminate and lithium silicate. These materials are obtained by the formation of only a transient liquid clathrate which quickly turns to solid aluminoxane compositions described as aluminoxanates.

The present invention forms stable, liquid clathrate aluminoxane compositions. The stable, liquid clathrate aluminoxane compositions show remarkable solubility and stability with no sign of gel formation even at higher concentrations than commercially available methylaluminoxane solutions. This permits the shipment and storage and use of concentrated (30 to 60 weight percent) MAO solutions.

In accordance with the invention there is provided a stable, liquid clathrate composition which comprises the reaction product, in an aromatic solvent, of an aluminoxane and an organic, inorganic or organometallic compound which is effective to form a stable, liquid clathrate composition with said aluminoxane.

Also provided is a process for preparing a methylaluminoxane composition which is substantially free of trimethylaluminum comprising (a) reacting a solution of methylaluminoxane, which contains a trimethylaluminum component, in an aromatic solvent with an organic, inorganic or organometallic compound which is effective to form a stable liquid clathrate composition with said methylaluminoxane so as to form a lower liquid methylaluminoxane containing clathrate layer and an upper, aromatic solvent layer which contains said trimethylaluminum component, and (b) separating said clathrate layer from said aromatic solvent layer.

Further, there is provided particulate solid aluminoxane-MX salt compositions obtained by removal of the aromatic inclusion solvent from the dense lower liquid layer of the liquid clathrate composition. Also, in accordance with the present invention polymerization catalyst systems are prepared using either the liquid clathrate aluminoxane salt compositions or the particulate solid aluminoxane-MX salt compositions, which can optionally be supported on solid carriers, in combination with co-catalysts such as metallocenes or transition or lanthanide metal compounds such as Ziegler/Natta type catalysts.

FIG. 1 is a graph showing three superimposed NMR spectra obtained from samples of a methylaluminoxane/toluene solution, a methylaluminoxane/toluene/KCl liquid clathrate solution and a methylaluminoxane/toluene/LiCl mixed clathrate solution.

Conventional methylaluminoxane solutions can be vacuum stripped to obtain solid methylaluminoxane. It is believed that this material exhibits fouling problems in slurry or particle form polymerization due to the presence of a significant amount of soluble aluminum compounds. The inventive solid aluminoxane salt compositions are virtually insoluble in aliphatic hydrocarbons and thus offer significant improvements with respect to reactor fouling.

Hydrocarbylaluminoxanes may exist in the form of linear or cyclic polymers with the simplest monomeric compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts are oligomeric materials, sometimes referred to as polyalkylaluminoxanes, which usually contain about 4 to 20 of the repeating units:

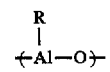

where R is $C_1$–$C_{10}$ alkyl and is preferably methyl. The exact structure of aluminoxanes has not been defined and they may contain linear, cyclic and/or cross-linked species. Methyl-aluminoxanes (MAOs) normally have lower solubility in organic solvents than higher alkylaluminoxanes and the methylaluminoxane solutions tend to be cloudy or gelatinous due to the separation of particles and agglomerates. In order to improve the solubility of the methylaluminoxane, higher alkyl groups, e.g. $C_2$ to $C_{20}$ can be included such as by hydrolyzing a mixture of trimethylaluminum with a $C_2$ to $C_{20}$ alkylaluminum compound such as, for example, triethyl-aluminum, tri-n-propylaluminum, triisobutylaluminum, tri-n-hexylaluminum, tri-n-octylaluminum or a triarylaluminum. Such mixed methyl-higher alkyl or aryl aluminoxanes are included in the term "methylaluminoxane" as used herein. Such modified methylaluminoxanes are described, for example, in U.S. Pat. No. 5,157,008. Besides MAO, non-limiting examples of hydrocarbylaluminoxanes for use in the invention include ethylaluminoxanes (EAO), isobutylaluminoxanes (IBAO), n-propylaluminoxanes, n-octylaluminoxanes, phenylaluminoxanes, and the like. The hydrocarbylaluminoxanes can also contain up to about 20 mole percent (based on aluminum) of moieties derived from amines, alcohols, ethers, esters, phosphoric and carboxylic acids, thiols, aryl disiloxanes, alkyl disiloxanes and the like to further improve activity, solubility and/or stability.

The aluminoxanes can be prepared as known in the art by the partial hydrolysis of hydrocarbylaluminum compounds. Any hydrocarbylaluminum compound or mixture of compounds capable of reacting with water to form an aluminoxane can be used. This includes, for example, trialkylaluminum, triarylaluminum, mixed alkyl aryl aluminum, and the like. The hydrocarbylaluminum compounds can be hydrolyzed by adding either free water or water containing solids, which can be either hydrates or porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4 \bullet 5H_2O$, $Al_2(SO_4)_3 \bullet 18H_2O$, $FeSO_4 \bullet 7H_2O$, $AlCl_3 \bullet 6H_2O$, $Al(NO_3)_3 \bullet 9H_2O$, $MgSO_4 \bullet 7H_2O$, $MgCl_2 \bullet 6H_2O$, $ZnSO_4 \bullet 7H_2O$, $Na_2SO_4 \bullet 10H_2O$, $Na_3PO_4 \bullet 12H_2O$, $LiBr$, $\bullet 2H_2O$, $LiCl \bullet 1H_2O$, $LiI \bullet 2H_2O$, $LiI \bullet 3H_2O$, $KF \bullet 2H_2O$, $NaBr \bullet 2H_2O$ and the like and alkali or alkaline earth metal hydroxide hydrates such as, for example, $NaOH \bullet H_2O$, $NaOH \bullet 2H_2O$, $BA(OH)_2 \bullet 8H_2O$, $KOH \bullet 2H_2O$, $CsOH \bullet 1H_2O$, $LiOH$, $\bullet 1H_2O$ and the like. Mixtures of any of the above hydrates can be used. The mole ratios of free water or water in the hydrate or in porous materials such as alumina or silica to total alkyl aluminum compounds in the mixture can vary widely, such as for example from about 2:1 to 1:4 with ratios of from about 4:3 to 1:3.5 being preferred.

Such hydrocarbylaluminoxanes and processes for preparing hydrocarbyl-aluminoxanes are described, for example, in U.S. Pat. Nos. 4,908,463; 4,924,018; 5,003,095; 5,041,583; 5,066,631; 5,099,050; 5,157,008; 5,157,137; 5,235,081; 5,248,801, and 5,371,260 whose entire teachings are incorporated herein by reference. The methyl-aluminoxanes contain varying amounts, of from about 5 to 35 mole percent, of the aluminum value as unreacted trimethylaluminum (TMA). The process of the invention removes most of this unreacted trimethylaluminum which can be recovered and re-used in making additional methylaluminoxane.

The novel, liquid clathrate aluminoxane compositions are prepared by the reaction of the aluminoxanes, especially methylaluminoxane, with organic, inorganic or organometallic compounds, and especially salts, which are potentially capable of dissociating or partially dissociating into cationic and anionic species (M-X species). Such reactions are characterized by the formation of two stable immiscible organic layers when carried out in an aromatic solvent. The appearance of the immiscible layers is termed liquid clathrate formation.

The reactions of trialkylaluminums with M-X species to produce the liquid clathrate phenomenon have been described by such authors as Atwood (Coordination Chemistry of Aluminum VCH Publishers, Inc. 1993, p. 197), Robinson (Coordination Chemistry Reviews, 112 (1992) 227) and Sangokoya (J. Incl. Phenom., 6 (1988) 263).

The reaction of MAO with M-X species was initially carried out in toluene in order to remove the TMA content via formation of a TMA liquid clathrate. Surprisingly, MAO was found to be more reactive towards M-X species than TMA. By analysis, the upper solvent layer consists mainly of TMA and toluene, while the lower liquid clathrate layer contains mainly MAO-MX and toluene with almost no titratable TMA content as shown by pyridine titration. This lower layer represents the stable, liquid clathrate aluminoxane salt composition embodiment of the invention.

MX compounds which are effective in forming stable, liquid clathrates with aluminoxanes are organic, inorganic or organometallic compounds which can potentially dissociate or partially dissociate into cationic and anionic components, especially in the presence of aluminoxanes. Non-limiting examples are alkali and alkaline earth halides or pseudohalides such as $KCl$, $KF$, $KOSiR_3$, $NaBO_4$, $NaF$, and the like. Pseudo-halides, which is term of art, are M-X salts where the anionic moieties are non-halogenides. The reactions of the compounds with MAO in aromatic solvents lead to the formation of liquid clathrate compositions. Other examples of MX compounds include metal hydrides such as $KH$, $LiH$ and alkyl, aryl and alkyl-aryl ammonium, phosphonium, sulfonium and other organometallic salts of halides and pseudo halides such as $Me_4NCl$, $MePh_3PBr$, $NaBPh_4$, $KB(C_6F_5)_4$, $LiR_4Al$, which will effectuate liquid clathrate formation by their reactions with MAO in aromatic solvents.

Also within the scope of this invention are organic, inorganic or organo-metallic materials which are not regarded as MX compounds per se but by virtue of their reaction with MAO act like MX compounds by the formation of stable, liquid clathrate aluminoxane compositions. A representative example of such compounds is triphenylphosphine oxide. Such compounds and their reaction products with aluminuminoxanes are included in the terms "MX compounds", "MX species" and "MX salt compositions", etc.

Non-limiting examples of suitable aromatic solvents include, toluene, benzene, xylenes, ethylbenzene, cumene, mesitylene, cymene and the like. The preferred solvent is toluene.

The clathrate forming compounds are preferably added in excess to the amount that dissolves to form the clathrate with the extra amount being easily removed, such as by filtration. About stoichiometric or lesser amounts are effective to form stable clathrates, depending upon the compound. Preferably, amounts of from about 0.01 to 0.5 moles of compound per mole of aluminum in the aluminoxane composition are added and more preferably from about 0.05 to 0.2 moles. The starting concentration of aluminoxane in solvent is not particularly critical and usually ranges from about 5 to 30 weight percent solution. As described herein, the weight percent of aluminoxane in the solutions is based on the total weight of aluminoxane and any unreacted trialkylaluminum in the solution. An advantage of the clathrates of the invention is that commercial MAO solutions are usually available as 5–20 wt. percent solutions in toluene. At higher concentrations, the inevitable limitations associated with solubility, stability and gel formation become extremely pronounced. Consequently, the transportation costs of the less concentrated solutions, especially to distant overseas places, significantly increase catalyst cost which in turn will push up polymer cost. In contrast, the inventive liquid clathrate aluminoxane-MX salt compositions can contain MAO in high concentrations, e.g. 30–60 wt. percent depending on the nature of the MX species. Furthermore, even at these high concentrations, the inventive liquid clathrate MAO-MX compositions are appreciably much more stable with respect to solubility, stability and gel formation compared to conventional MAO solutions.

The reaction temperature is chosen to provide a stable, liquid clathrate. By a stable liquid clathrate is meant that the two immiscible liquid layer systems remain intact such that the upper solvent layer can be separated from the lower clathrate layer. Although the use of ambient temperatures is most convenient (i.e. from about 15° to 30° C.), some compounds require elevated temperatures of up to 80° C. or higher in order to form a stable, liquid clathrate. A suitable temperature for any particular compound can be experimentally determined.

Removal of solvent from the dense lower liquid clathrate layer such as by vacuum distillation or the addition of excess non-aromatic solvent results in the isolation of solid, particulate aluminoxane salt compositions. The solid, particulate MAO-MX salt compositions are virtually insoluble in aliphatic hydrocarbons. When introduced into aromatic solvents, the novel MAO-MX salt will incorporate as much solvent as required to reform a liquid clathrate (inclusion solvent) which separates out from the rest of the solvent resulting again in two immiscible liquid layers.

The aluminoxane MX composition can be used in combination with metallocenes and/or transition metal compounds to provide olefin polymerization catalysts.

A notable result of liquid clathrate formation is that the aluminoxane-MX product contains essentially no trimethylaluminum as indicated by pyridine titration. It should also be noted that the variability in trimethylaluminum content of methyl-aluminoxane is probably the major source of inconsistency in previously known supported catalyst systems. Therefore, this invention provides a means to avoid this inconsistency.

As used in this application, the term "metallocene" includes metal derivatives which contain at least one cyclopentadienyl moiety. Suitable metallocenes are well known in the art include the metallocenes of Groups 3, 4, 5, 6, lanthanide and actinide metals, for example, the metallocenes which are described in U.S. Pat. Nos. 2,864,843; 2,983,740; 4,665,046; 4,874,880; 4,892,851; 4,931,417; 4,952,713; 5,017,714; 5,026,798; 5,036,034; 5,064,802; 5,081,231; 5,145,819; 5,162,278; 5,245,019; 5,268,495; 5,276,208; 5,304,523; 5,324,800; 5,329,031; 5,329,033; 5,330,948, 5,347,025; 5,347,026; and 5,347,752, whose teachings with respect to such metallocenes are incorporated herein by reference.

Non-limiting illustrative examples of such metallocenes are bis(cyclopenta-dienyl)zirconium dimethyl, bis (cyclopentadienyl)zirconium dichloride, bis(cyclopentadienyl)zirconium monomethylmonochloride, bis (cyclopentadienyl)titanium dichloride, bis (cyclopentadienyl)titanium difluoride, cyclopentadienylzirconium tri-(2-ethylhexanoate), bis (cyclopentadienyl)zirconium hydrogen chloride, bis (cyclopentadienyl)hafnium dichloride, racemic and meso dimethylsilanylene-bis(methylcyclopentadienyl)hafnium dichloride, racemic dimethylsilanylene-bis(indenyl)hafnium dichloride, racemic ethylene-bis(indenyl)zirconium dichloride, ($\eta^5$-indenyl)hafnium trichloride, ($\eta^5$-$C_5Me_5$) hafnium trichloride, racemic dimethylsilanylene-bis (indenyl)thorium dichloride, racemic dimethylsilanylene-bis(4,7-dimethyl-1-indenyl)zirconium dichloride, racemic dimethylsilanylene-bis(indenyl)uranium dichloride, racemic dimethylsilanylene-bis(2,3,5-trimethyl-1-cyclopentadienyl) zirconium dichloride, racemic dimethylsilanylene(3-methylcyclopentadienyl)hafnium dichloride, racemic dimethylsilanylene-bis(1-(2-methyl-4-ethylindenyl zirconium dichloride; racemic dimethylsilanylene-bis(2-methyl-4,5,6,7-tetrahydro-1-indenyl)-zirconium dichloride, bis (pentamethylcyclopentadienyl)thorium dichloride, bis-(pentamethylcyclopentadienyl)uranium dichloride, (tert-butylamido)dimethyl(tetramethyl-$\eta^5$-cyclopentadienyl) silanetitanium dichloride, (tert-butylamido)dimethyl (tetramethyl-$\eta^5$-cyclopentadienyl)silanechromium dichloride, (tert-butylamido)dimethyl($\eta^5$-cyclopentadienyl) silanetitanium dichloride, (tert-butylamido)dimethyl (tetramethyl-$\eta^5$-cyclopentadienyl)silanemethyltitanium bromide, (tert-butylamido)(tetramethyl-$\eta^5$-cyclopentadienyl)-1,2-ethanediyluranium dichloride, (tert-butylamido)(tetramethyl-$\eta^5$-cyclopentadienyl)-1,2-ethanediyltitanium dichloride, (methylamido)(tetramethyl-$\eta^5$-cyclopentadienyl)-1,2-ethanediylcerium dichloride, (methylamido)(tetramethyl-$\eta^5$-cyclopentadienyl)-1,2-ethanediyltitanium dichloride, (ethylamido)(tetramethyl-$\eta^5$-cyclopenta-dienyl)methylenetitanium dichloride, (tert-butylamido)dibenzyl(tetramethyl-$\eta^5$-cyclopentadienyl)-silanebenzylvanadium chloride, (benzylamido)dimethyl (indenyl)silanetitanium dichloride, and (phenylphosphido) dimethyl(tetramethy$\eta^5$-cyclopentadienyl) silanebenzyltitanium chloride.

Suitable transition metal or lanthanide compounds include the well known Ziegler-Natta catalyst compounds of Group 4–6 metals. Non-limiting illustrative examples of such compounds include $TICl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_{17})_2Br_2$, $VCl_4$, $VOCl_3$, $VO(OC_2H_5)_3$, $ZrCl_4$, $ZrCl_3{}_{(OC_2H_5)}$, $Zr(OC_2H_5)_4$ and $ZrCl(OC_4H_9)_3$ and the like.

The molar proportions of metallocene and/or transition metal or lanthanide compound in the catalyst composition to the aluminum derived from the aluminoxane in the aluminoxane-MX composition are selected to provide the desired degree of polymerization activity and generally range from about $1\times10^{-1}$ to $1\times10^{-4}$ to 1 and preferably from about $2\times10^{31}{}^{1}$ to $5\times10^{-4}$ to 1.

Either the liquid clathates or the solid aluminoxane-MX compositions can be used to prepare catalysts.

The metallocenes or transition or lanthanide compounds can be supported on the novel aluminoxane compositions. Also, the reaction of MAO-MX compositions with metallocene and the like could be carded out in the presence of other organic or inorganic substrates such as silica, alumina and other support substrates which are known in the art as suitable support materials. The aluminoxane-MX composition can be initially reacted with the metallocenes and then with the support substrate or the aluminoxane-MX compositions can be reacted with the support substrate and then with the metallocenes and vice versa. In addition, the original aluminoxane compound can be initially modified by treatment with an $R_3Al$ compound or mixtures thereof or treated with other reagents which do not result in an appreciable deterioration of the polymerization capability of the aluminoxane before being treated with the MX species in order to form the aluminoxane-MX clathrate compositions.

The catalysts are effective to produce olefin polymers and especially ethylene polymers, propylene polymers and ethylene/α-olefin copolymers. Examples of olefins that can be polymerized in the presence of the catalysts of the invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Polymerization of ethylene or copolymerization with ethylene and an α-olefin having 3 to 10 carbon atoms is preferable. Such polymerizations may be performed in either the gas or liquid phase (e.g. in a solvent, such as toluene, or in a diluent, such as heptane). The polymerization can be conducted at conventional temperatures (e.g., 0° to 250° C.) and pressures (e.g., ambient to 50 kg/cm$^2$) using conventional procedures as to molecular weight regulation and the like.

The invention is further illustrated by, but is not intended to be limited to, the following examples.

All experiments were performed under inert atmosphere condition. Schlenk vacuum line and glasswares, in conjunction with dry N2-box were employed to handle all air sensitive materials. Reagents were obtained from commercial sources without further purification. Aluminoxane samples were obtained from stock solutions produced by Albemarle Corporation. Solvents were dried and distilled by standard methods.

EXAMPLE 1

MAO/Tol/KCl

A solution of methylaluminoxane (135 g, 648 mmol Al) in toluene (Tol) was placed in a reaction bottle. Potassium chloride (2.42 g, 32.4 mmol) was added and the mixture was stirred at room temperature. After about one hour, clathrate formation was observed. Within three hours, all solid (KCl) dissolved. More KCl (1.21 g) was then added and the mixture was stirred at room temperature overnight. Again, all solid dissolved. More KCl (1.21 g) was then added, almost all of which reacted within a few hours. The total amount of KCl added was about 10 mole percent of the total aluminum value of the original MAO solution.

The liquid, two phase system was filtered through a medium frit to remove any unreacted KCl. Then the clathrate solution was separated using a separating funnel. The dense lower phase contained no TMA by pyridine titration. The lighter upper phase was shown by gas evolution measurement to contain mostly TMA (gas/Al ratio~3). Furthermore, proton NMR of the upper layer showed only the TMA peak, the broad MAO peak was not observed.

EXAMPLE 2

MAO/Tol/KF

MAO/Tol (87 g, 382 mmol Al) was placed in a reaction bottle and then treated with potassium fluoride (KF, 2.22 g, 38.2 mmol). The mixture was stirred at room temperature overnight (15 hours). All the solid appeared to have dissolved with formation of liquid clathrate. The mixture was filtered through a coarse frit.

EXAMPLE 3

MAO/Tol/NaF

A reaction bottle was filled with MAO solution (91 g, 400 mmol Al) in toluene and sodium fluoride (NaF, 1.7 g, 40 mmol) was added. The mixture was stirred overnight at room temperature. A liquid clathrate resulted, but the lower layer was extremely thick, and some unreacted NaF could be seen at the bottom. The syrupy lower layer was too thick to be filtered. It was, therefore, decanted to remove the unreacted NaF. The resulting product was heated at 80° C. (oil bath) for about six hours. While hot, the lower layer was free flowing, but as soon as it cooled down, it became syrupy again.

EXAMPLE 4

MAO/TOl/Me$_4$NCl

A toluene solution of MAO (51.3 g, 178 mmol Al) was treated with tetramethylammonium chloride (Me$_4$NCl, 2.93 g, 26.8 mmol). The mixture was stirred at room temperature overnight. A condensed methylaluminoxane-amine complex composition resulted. The two layer liquid system was filtered to give a lower dense layer which contained all the MAO product (23 g) and the upper layer which contained all the TMA.

EXAMPLE 5

MAO/Tol/MePh$_3$PBr

Methyltriphenylphosphonium bromide (MePh$_3$PBr, 5.93 g, 16.6 mmol) was added to an MAO solution (47.7 g, 166 mmol Al) in toluene. After stirring for about 2 hours, a three layered liquid clathrate resulted. More toluene (40 ml) was added. The mixture was then stirred overnight to give only a two layer clathrate solution. The mixture was filtered and separated to give a viscous lower layer (27 g) and a non-viscous upper layer (47 g).

The proton NMR of the upper layer showed only TMA and no phosphine or MAO.

EXAMPLE 6

MAO/Tol/NaBPh$_4$

An MAO solution (80 g, 352 mmol Al) in toluene was treated with sodium tetraphenylborate (NaBPh$_4$, 3 g, 8.8 mmol) and the mixture was stirred overnight. No clathrate was formed and only a fraction of the solid borate dissolved. On heating at 80° C. (oil bath) for about one hour, all the solid dissolved but no clathrate was formed. When the mixture was allowed to cool to room temperature, still no clathrate formation was observed. More borate salt (3 g) was added such that total amount of borate salt is about 5 mole percent of the total aluminum value in the original MAO solution. The mixture was heated at 90° C. (oil bath) for about two hours and most of the solid dissolved but no clathrate was observed while hot. On cooling overnight, clathrate formation was observed. The mixture was filtered to remove any solid residue.

EXAMPLE 7

MAO/Tol/KOSiMe$_3$

To a solution of MAO (109 g, 525 mmol Al) was added potassium trimethylsilanolate (KOSiMe$_3$, 5.1 g, 39.4 mmol) in batches. Some gas evolution was observed. The reaction was also exothermic. This mixture was stirred at room temperature overnight and a two liquid layer system resulted. The lower dense layer seemed to contain some solid residue. The mixture was filtered to give clear, liquid two layer system. The lower layer contained the condensed methylaluminoxane silanolate complex composition.

EXAMPLE 8

MAO/Tol/KH

A toluene solution of MAO (86 g, 353 mmol Al) was placed in a reaction bottle and potassium hydride (KH, 0.8 g, 20 mmol) was added in batches. Slowly, the solid KH dissolved and a liquid clathrate separated to give a condensed methylaluminoxane complex composition within 30 minutes. The mixture was stirred at room temperature overnight (14 hours). Almost all the solid dissolved. The mixture was filtered to remove any solid residue.

EXAMPLE 9

MAO/Tol/Ph3P(O)

An MAO solution (71 g, 291 mmol Al) was placed in a reaction bottle. Triphenylphosphine oxide (6.5 g, 23.3 mmol) was added. The mixture was stirred at room temperature to give liquid clathrate formation containing the new condensed methylaluminoxane phosphonium complex composition. The mixture was filtered to remove any trace of solid residue.

COMPARATIVE EXAMPLES

COMPARATIVE EXAMPLE 1

MAO/Tol/LiCl

An MAO solution (225 g, 1080 mmol Al) was treated with lithium chloride (4.6 g, 108 mmol). The mixture was stirred at room temperature for 4 days and no clathrate was formed. Then the mixture was heated at 90° C. (oil bath) for 2 hours and still no clathrate was formed. The mixture was filtered through a medium frit. ICP analysis showed that lithium had been incorporated into the MAO product (228 ppm) while the product appeared to be more stable to gel formation no clathrate formation was observed.

COMPARATIVE EXAMPLE 2

MAO/Tol/LiF

A toluene solution of MAO (94.7 g, 454.6 mmol Al) was placed in a reaction bottle and then lithium fluoride (LiF, 1.18 g, 45.46 mmol) was added. The mixture was stirred at room temperature for 3 days. No clathrate formation was observed. However, ICP analysis, Li-7 and F-19 NMR confirmed incorporation of LiF into the MAO composition (646 ppm Li by ICP).

EXAMPLE 10

MAO/Tol/LiCl (Excess LiCl and Heat)

This experiment showed that clathrate formation could be forced by using excess LiCl and heating over a long period. However, the clathrate formation was not as clear cut as in the regular clathrate compositions as described above.

Methylaluminoxane solution (98 g, 441 mmol Al) was treated with LiCl (3.8 g, 88 mmol) and then heated at 90° C. for 24 hours. No clathrate was seen when hot. On cooling, a small amount of lower phase separated. Analysis, however, did not show the usual clear cut separation of MAO and TMA. Thus, pyridine titration showed the presence of TMA both in the lower and upper phases.

Furthermore, Al-27 NMR confirmed the mixed clathrate formation composed of MAO/TMA complex (159 ppm) and MAO/LiCl complex (−13 ppm). Note that regular MAO solution in toluene usually shows a peak at about 155 ppm referenced to external 1M $AlCl_3$ solution in water.

EXAMPLE 11

MAO/Tol/LiH (Supported on Silica)

Lithium hydride (0.2 g, 25 mmol) was added in batches, to an MAO solution in toluene (71 g, 291 mmol Al). Surprisingly, no gas evolution was evident. The mixture was stirred overnight at room temperature. A lower thick and almost immobile phase separated. The clathrate composition was then heated at 80° C. for about 2 hours. On cooling to room temperature, silica gel (14 g) was added in batches. As the silica reacted with the lower phase, the later slowly became mobile again and the stirrer bar started to turn again. The mixture was stirred overnight at room temperature after which, the mixture was heated at 60° C. for one hour. Additional solvent (heptane, 50 ml) was added in order to allow quantitative transfer to another reaction bottle. At this point, the mixture was heated at 80° C. for 2 hours and then filtered to obtain the clathrate composition supported on silica.

REACTIONS WITH METALLOCENE

EXAMPLE 12

The product of Example 1 was treated with zirconocene dichloride (3.5 g, 12 mmol Zr). The clear solution slowly turned colored on stirring at room temperature. After a few hours, all the solid dissolved and the upper layer had a darker orange brown color while the dense lower layer was only yellowish. The mixture was stirred overnight (14 hours) at room temperature. Reversed coloration was observed, the dense lower layer became dark orange while the upper layer turned only slightly yellowish. The mixture was filtered to remove any solid residue. The dense lower layer was separated using a separatory funnel to give 39 g dark orange dense solution. Heptane (80 g) was then added to give a yellowish brown slurry. After stirring for about one hour, the mixture was filtered to give yellowish brown solid product (23 g). This was then dried in vacuo to give 20 g solid product. Analysis by ICP showed Al/Zr=58 and Al/K=12.

EXAMPLE 13

The product of Example 2 was treated with zirconocene chloride (0.2 g, 0.68 mmol Zr) as described in Example 10. After drying, a yellowish powder (19 g) was recovered.

EXAMPLE 14

The product of Example 7 was allowed to react with zirconocene dichloride (1.5 g, 5.1 mmol Zr) as described in Example 10, to give, on drying, orange brown powder (28 g). Analysis by ICP gave Al/Zr=87 ad Al/K=14.

EXAMPLE 15

The product of Example 6 was treated with zirconocene dichloride (0.2 g, 0.68 mmol Zr) as described in Example 10 above to give dried orange brown powder.

EXAMPLE 16

Ethylene Polymerization

In order to demonstrate the utility of these novel aluminoxane compositions, the products of Examples 14 and 15 were used in ethylene polymerization.

The polymerization tests were conducted in a Parr reactor (600 ml) containing heptane (300 ml) at 90 psi of ethylene pressure and 90° C. during a period of about 30 minutes. Solid catalyst (0.2 g) was used in each case to obtain 16 g and 21 g of polymer respectively in the presence of TMA (2 mmol). The calculated specific activities for the polymerization reactions were 2.11 and $2.74 \times 10^4$ gPE/mol Zr.Atm.hr respectively. The above polymerization conditions for these novel catalyst compositions have not been optimized.

Further appreciation of the invention is graphically illustrated by the Al-27 NMR spectra of FIG. 1. The spectra were obtained using an aluminum background free probe described by Dr. L. S. Simeral in Applied Spectroscopy Vol. 47, p. 1954 (1994).

Curve o is Al-27 NMR spectrum of regular MAO (MAO/TMA complex) solution in toluene. The major peak is a 155 ppm relative to external 1M $AlCl_3$ in $H_2O$.

Curve ● is the spectrum of MAO/KCl clathrate solution with the only peak at −10 ppm. The designation LL means lower layer.

Curve □ is the spectrum of MAO/LiCl mixed complex formation (clathrate) with 2 major peaks at 159 ppm and −13 ppm. The former peak corresponds to MAO/TMA complex and the later peak corresponds to MAO/LiCl complex, both complexes being present in the lower layer of the mixed liquid clathrate formation.

What is claimed is:

1. A liquid clathrate composition which comprises the reaction product, in an aromatic solvent, of an aluminoxane and an organic, inorganic or organometallic compound which is effective to form a stable, liquid clathrate composition with said aluminoxane.

2. The composition of claim 1 wherein said compound is an organic, inorganic or organometallic salt which can at least partially dissociate into cationic and anionic species in said solvent.

3. An aluminoxane clathrate composition which comprises methylaluminoxane, M-X species derived from an organic, inorganic or organometallic compound which is effective to form a stable clathrate with said methylaluminoxane, and an aromatic inclusion solvent.

4. The composition of claim 3 wherein said methylaluminoxane is an oligomeric methylaluminoxane and said compound is an organic, inorganic or organometallic salt or hydride.

5. The composition of claim 4 wherein said salt is selected from the group consisting of KCl, KF, NaF, KH, LiH, $KOSiR_3$, $NaBPh_4$, $Me_4NCl$, $MePh_3PBr$, and $KB(C_5F_5)_4$.

6. A solid, methylaluminoxane-MX salt composition obtained by removing the aromatic inclusion solvent from the clathrate composition of claim 3.

7. A process for preparing a methylaluminoxane composition which is substantially free of trimethylaluminum comprising (a) reacting a solution of trimethylaluminum and methylaluminoxane in an aromatic solvent with an organic, inorganic or organometallic compound which is effective to form a stable, liquid clathrate with said methylaluminoxane so as to form a lower, liquid methylaluminoxane containing clathrate layer and an upper, aromatic solvent layer which contains said trimethylaluminum, and (b) separating said clathrate layer from said aromatic solvent layer.

\* \* \* \* \*